(12) United States Patent
Zukowski

(10) Patent No.: US 11,707,369 B2
(45) Date of Patent: Jul. 25, 2023

(54) FLEXIBLE ENDOLUMINAL DEVICE

(71) Applicant: W. L. Gore & Associates, Inc., Newark, DE (US)

(72) Inventor: Stanislaw L. Zukowski, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 512 days.

(21) Appl. No.: 16/839,988

(22) Filed: Apr. 3, 2020

(65) Prior Publication Data

US 2020/0229951 A1 Jul. 23, 2020

Related U.S. Application Data

(63) Continuation of application No. 15/459,824, filed on Mar. 15, 2017, now Pat. No. 10,639,177, which is a continuation of application No. 14/079,353, filed on Nov. 13, 2013, now Pat. No. 9,629,735.

(60) Provisional application No. 61/727,585, filed on Nov. 16, 2012.

(51) Int. Cl.
| | |
|---|---|
| *A61F 2/89* | (2013.01) |
| *A61M 25/00* | (2006.01) |
| *A61F 2/07* | (2013.01) |
| *A61F 2/852* | (2013.01) |

(52) U.S. Cl.
CPC .............. *A61F 2/89* (2013.01); *A61F 2/07* (2013.01); *A61F 2/852* (2013.01); *A61M 25/0054* (2013.01); *A61F 2250/0019* (2013.01); *A61F 2250/0029* (2013.01); *A61F 2250/0039* (2013.01); *A61F 2250/0063* (2013.01); *A61F 2250/0098* (2013.01)

(58) Field of Classification Search
CPC ............... A61F 2/07; A61F 2250/0039; A61F 2250/0063; A61F 2/852; A61F 2250/0019; A61F 2250/0029; A61F 2250/0065

See application file for complete search history.

(56) References Cited

U.S. PATENT DOCUMENTS

| | | |
|---|---|---|
| 4,973,189 A | 11/1990 | Bechtold |
| 5,522,881 A | 6/1996 | Lentz |
| 6,042,605 A | 3/2000 | Martin et al. |
| 6,911,040 B2 | 6/2005 | Johnson et al. |
| 7,637,939 B2 | 12/2009 | Tischler |
| 7,704,275 B2 | 4/2010 | Schmid et al. |
| 7,846,195 B2 | 12/2010 | Berra et al. |
| 7,918,884 B2 | 4/2011 | Majercak et al. |

(Continued)

FOREIGN PATENT DOCUMENTS

| | | |
|---|---|---|
| EP | 1779809 A1 | 5/2007 |
| EP | 2151217 A1 | 2/2010 |

(Continued)

OTHER PUBLICATIONS

International Search Report and Written Opinion received for PCT Patent Application No. PCT/US2019/029976, dated Jul. 1, 2019, 12 pages.

(Continued)

*Primary Examiner* — Katherine M Shi

(57) ABSTRACT

The present disclosure describes endoluminal devices, such as stents and stent grafts capable of being bent smoothly, with various benefits resulting therefrom.

13 Claims, 3 Drawing Sheets

(56) References Cited

U.S. PATENT DOCUMENTS

| | | |
|---|---|---|
| 7,951,188 B2 | 5/2011 | Ainsworth et al. |
| 8,480,725 B2 | 7/2013 | Rasmussen et al. |
| 9,629,735 B2 | 4/2017 | Zukowski |
| 2001/0020181 A1 | 9/2001 | Layne |
| 2001/0049550 A1* | 12/2001 | Martin ............... A61F 2/95 623/1.13 |
| 2001/0049554 A1 | 12/2001 | Ruiz et al. |
| 2003/0088305 A1* | 5/2003 | Van Schie ............. A61F 2/06 623/1.12 |
| 2005/0154448 A1 | 7/2005 | Cully et al. |
| 2006/0155364 A1 | 7/2006 | Holloway et al. |
| 2006/0195172 A1 | 8/2006 | Luo et al. |
| 2006/0259123 A1 | 11/2006 | Dorn |
| 2007/0142902 A1 | 6/2007 | Yadin |
| 2007/0208413 A1 | 9/2007 | Nakano |
| 2008/0009932 A1 | 1/2008 | Ta et al. |
| 2008/0023103 A1 | 1/2008 | Ballinger |
| 2008/0039926 A1 | 2/2008 | Majercak et al. |
| 2008/0103589 A1 | 5/2008 | Cheng et al. |
| 2009/0048663 A1 | 2/2009 | Greenberg |
| 2009/0163996 A1* | 6/2009 | Bregulla ............. A61F 2/915 623/1.16 |
| 2009/0210049 A1 | 8/2009 | Thielen et al. |
| 2009/0306763 A1 | 12/2009 | Roeder et al. |
| 2010/0234932 A1 | 9/2010 | Arbefeuille et al. |
| 2010/0286760 A1 | 11/2010 | Beach et al. |
| 2011/0087318 A1 | 4/2011 | Daugherty et al. |
| 2011/0144736 A1 | 6/2011 | Prabhu et al. |
| 2011/0144737 A1 | 6/2011 | Burgermeister et al. |
| 2011/0144738 A1 | 6/2011 | Casey |
| 2011/0213455 A1 | 9/2011 | Obradovic et al. |
| 2012/0330402 A1* | 12/2012 | Vad ................... A61F 2/88 623/1.13 |
| 2013/0197657 A1* | 8/2013 | Anca .................. A61F 2/07 623/23.7 |
| 2014/0142684 A1 | 5/2014 | Zukowski |
| 2017/0181874 A1 | 6/2017 | Zukowski |
| 2021/0052404 A1 | 2/2021 | Irwin et al. |

FOREIGN PATENT DOCUMENTS

| | | |
|---|---|---|
| JP | 2002-536057 A | 10/2002 |
| JP | 2003-245359 A | 9/2003 |
| JP | 2007-506493 A | 3/2007 |
| JP | 2009-131397 A | 6/2009 |
| JP | 2011-508625 A | 3/2011 |
| JP | 2012-520153 A | 9/2012 |
| JP | 2012-524641 A | 10/2012 |
| JP | 2013-507194 A | 3/2013 |
| WO | 98/51186 A1 | 11/1998 |
| WO | 01/06952 A1 | 2/2001 |
| WO | 2004/047687 A1 | 6/2004 |
| WO | 2005/016793 A1 | 2/2005 |
| WO | 2008/130572 A1 | 10/2008 |
| WO | 2009/082444 A1 | 7/2009 |
| WO | 2010/105195 A2 | 9/2010 |
| WO | 2011/044459 A2 | 4/2011 |
| WO | 2012/092627 A1 | 7/2012 |

OTHER PUBLICATIONS

International Search Report for PCT/US2013/070132 dated Feb. 6, 2014, corresponding to U.S. Appl. No. 14/079,353, 5 pages.
International Preliminary Report on Patentability received for PCT Patent Application No. PCT/US2013/070132, dated May 28, 2015, 8 pages.
International Written Opinion received for PCT Patent Application No. PCT/US2013/070132, dated Feb. 6, 2014, 6 pages.

* cited by examiner

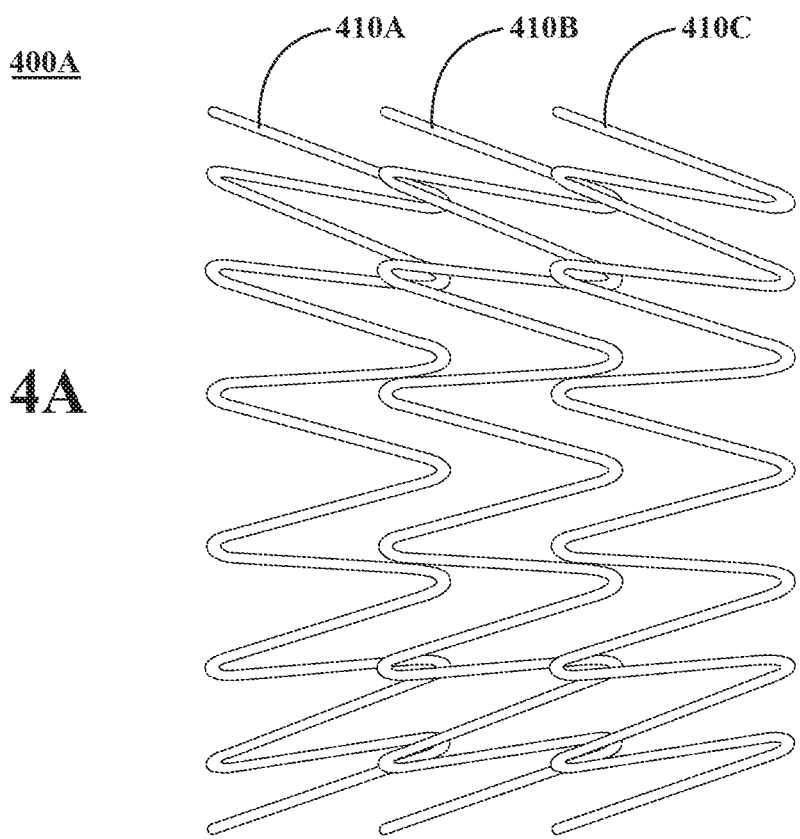
FIG. 4A
FIG. 4B
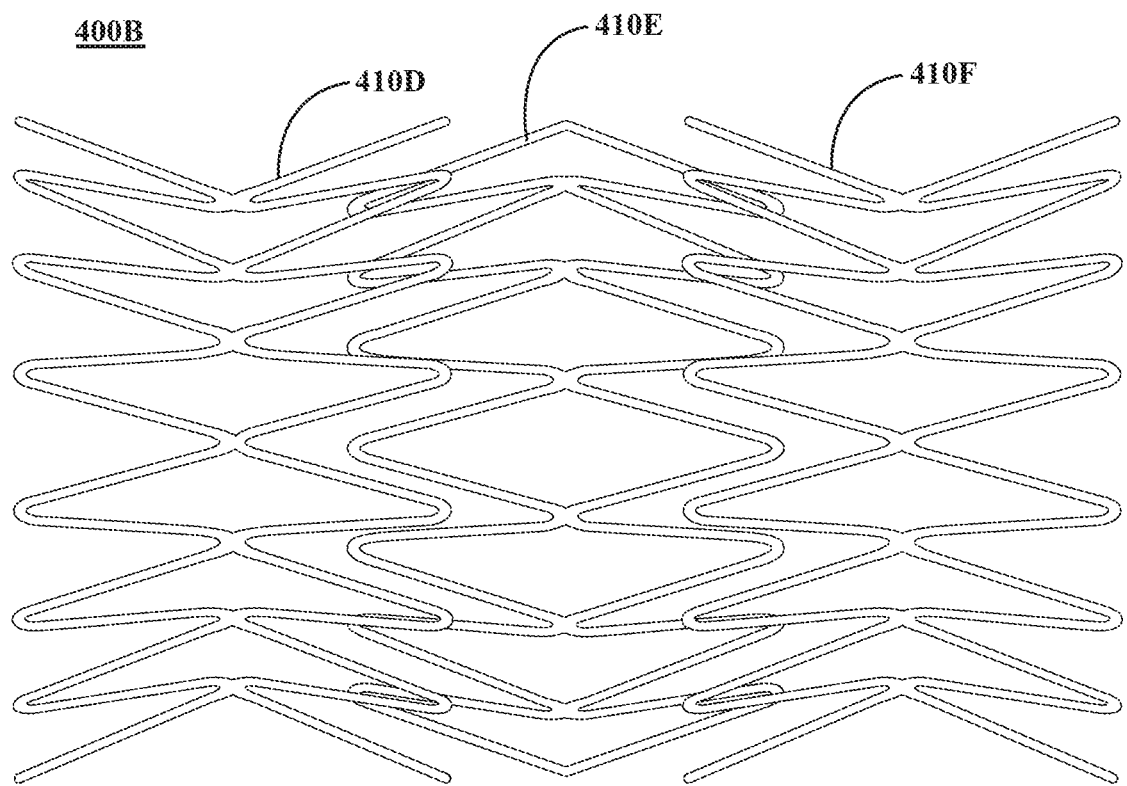

FLEXIBLE ENDOLUMINAL DEVICE

CROSS-REFERENCE TO RELATED APPLICATION

This application is a continuation of U.S. patent application Ser. No. 15/459,824, filed Mar. 15, 2017, entitled FLEXIBLE ENDOLUMINAL DEVICE, which is a continuation of U.S. patent application Ser. No. 14/079,353, filed Nov. 13, 2013, entitled FLEXIBLE ENDOLUMINAL DEVICE, now U.S. Pat. No. 9,629,735, issued Apr. 25, 2017, which claims the benefit of U.S. Provisional Application 61/727,585, filed Nov. 16, 2012, entitled FLEXIBLE ENDOLUMINAL DEVICE, all of which are incorporated herein by reference in their entireties for all purposes.

FIELD

The present disclosure relates generally to endoluminal devices and, more specifically, to endoluminal devices such as stents and stent grafts capable of being bent smoothly.

BACKGROUND

Endoluminal devices such as stents, stent grafts, catheters, filters, valves, anchors, occluders, and other implantable devices are frequently used to treat the vasculature of mammalian patients. Such devices often include a frame comprising a stent which may be used alone or in connection with other materials such as graft or filtering materials. It may be desirable that the stent be capable of flexing as it is bent within the vasculature and thus, bend smoothly without producing a kink. For example, it may be desirable that the stent be capable of nesting as it is bent within the vasculature and thus, bend smoothly. Thus, there is a need for stents that provide such characteristics.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein:

FIG. 4A illustrates a close-up side view of adjacent nested rings having the same profile in accordance with the present disclosure; and FIG. 4B illustrates a close-up side view of adjacent nested rings having alternating profiles in accordance with the present disclosure.

DETAILED DESCRIPTION OF THE ILLUSTRATED EMBODIMENTS

Figure 1A:
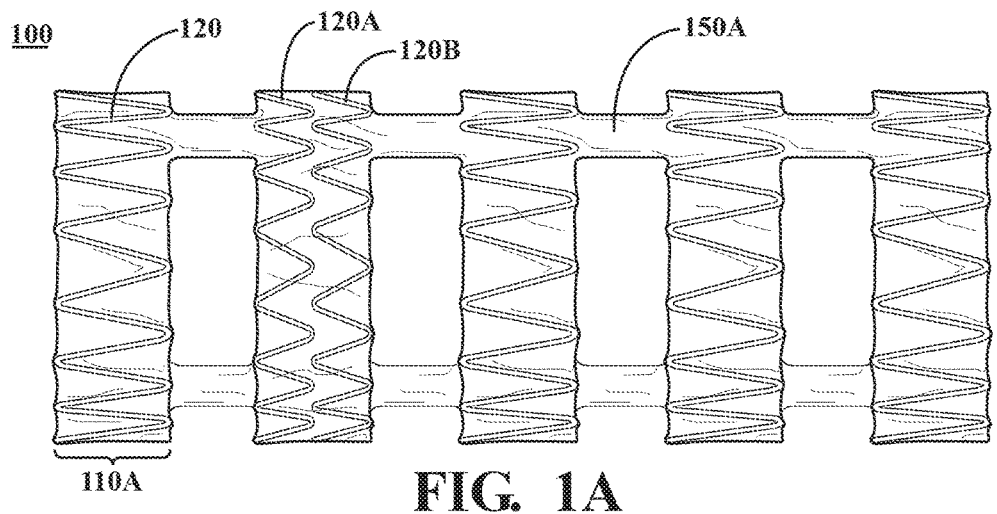
FIG. 1A illustrates a side view of a stent in accordance with the present disclosure.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure can be described in connection with various principles and beliefs, the present disclosure should not be bound by theory.

Endoluminal devices such as stents, stent grafts, catheters, filters, valves, anchors, occluders, and other implantable devices are frequently used to treat the vasculature of mammalian patients. Such devices often include a frame comprising a stent which may be used alone or in connection with other materials such as graft or filtering materials.

Figure 1B:
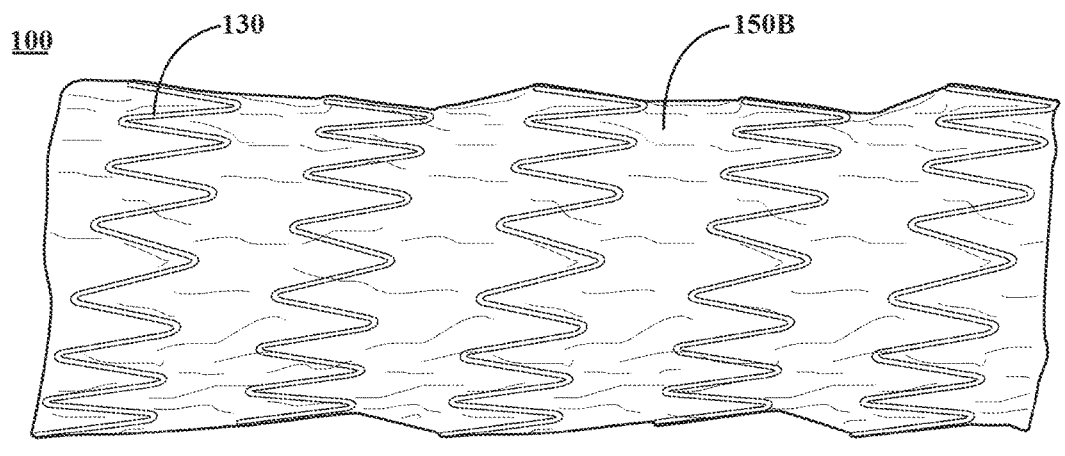
FIG. 1B illustrates a side view of a stent graft in accordance with the present disclosure.

With reference to FIGS. 1A and 1B, a stent 100 is a generally tube like structure that defines a lumen and that is inserted into the vasculature to open and/or maintain the vasculature in order to prevent or address localized flow constriction, weakening of the vasculature wall, aneurisms, etc. In this regard, the stent 100 can be comprised of a plurality of hoops (e.g., as illustrated in FIG. 1A), can have a helical configuration (e.g., as illustrated in FIG. 1B), can be cut from a tube, etc.

As used herein, a ring 110A,B of the stent 100 is a longitudinal section thereof which can comprise one or more hoops 120, helical windings 130, etc. For instance, a ring 110A may broadly comprise a single hoop 120 or two or more hoops 120A,B. Likewise, a ring 110B may broadly comprise a single helical winding 130 or two or more helical windings (not shown). Hoops 120 and helical windings 130 may include various further patterns along their length such as undulating patterns with angular apical areas interconnected by generally straight sections, zig-zag patterns, diamond patterns, etc. As used herein in relation to a stent, luminal refers to an interior of a stent, while abluminal refers to an exterior of a stent.

In some embodiments, the stent 100 is comprised of a shape-memory material, such as, but not limited to, nitinol. In other embodiments, the stent 100 can be compressible. In yet other embodiments, the stent 100 can be comprised of other materials, self-expandable or otherwise expandable (e.g., with a balloon or spring mechanism), such as various metals (e.g., stainless steel), alloys and polymers.

Adjacent rings of the stent 100 (including individual hoops 120 and helical windings 130) can be coupled with one or more interconnections 150A,B, which can be comprised of various materials now known or as yet unknown. For example, such interconnection materials can comprise any number of biocompatible materials, such as, for example, expanded polytetrafluoroethylene (ePTFE), expanded modified PTFE, and expanded copolymers of PTFE, fluorinated ethylene propylene (FEP), polyester, polyurethane, fluoropolymers, such as perfouorelastomers and the like, polytetrafluoroethylene, silicones, urethanes, ultra high molecular weight polyethylene, aramid fibers, other polymeric materials, and combinations thereof.

The interconnections 150A,B can be in contact with an abluminal and/or luminal surface of the stent 100. The interconnection 150B can cover all or a substantial portion of a longitudinal surface of the stent 100 (e.g., in connection with an endoluminal graft as illustrated in FIG. 1B or an endoluminal filter). In alternate embodiments, one or more of the interconnections 150A can couple adjacent rings 110A of the stent 100 at one or more discrete locations (e.g., in connection with the stent 100 as illustrated in FIG. 1A). In this regard, adjacent rings of the stent 100 coupled with one or more of the interconnections 150A,B can be used in connection with a wide variety of endoluminal devices such as stent grafts, catheters, filters, valves, anchors, occluders, and other implantable devices.

Figure 2A:
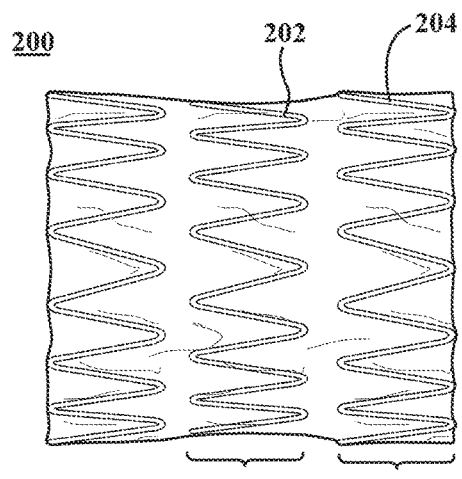
FIG. 2A illustrates a close-up view of circumferentially uniform nested rings in accordance with the present disclosure.
Figure 2B:
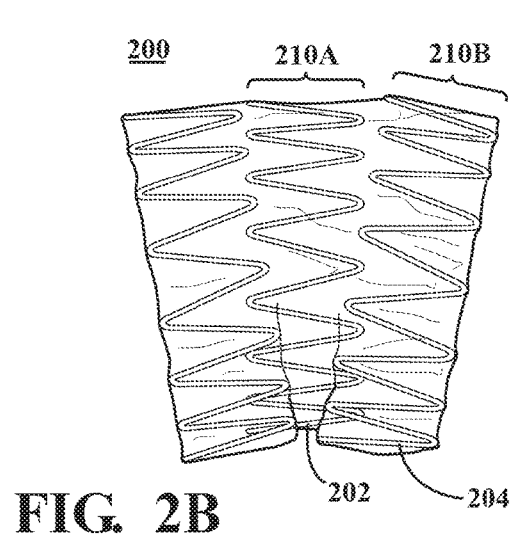
FIG. 2B illustrates a close-up view of circumferentially non-uniform nested rings in accordance with the present disclosure.

In various embodiments, and with reference to FIGS. 2A and 2B, a stent 200 is capable of nesting as it is bent within the vasculature, which may in turn facilitate smooth bending of the stent 200.

The terms "smooth" and "smoothly" as used herein in relation to the bending of an endoluminal device or a stent refers to a change in luminal direction while substantially maintaining the patency of the lumen, for example, without kinking the lumen.

As used herein, nesting refers to the relative movement of a ring 210A of the stent 200 with respect to an adjacent ring 210B of the stent 200 in a telescoping fashion, whereupon at least a portion of an abluminal surface 202 of the ring 210A of the stent 200 faces at least a portion of a luminal surface 204 of the adjacent ring 210B of the stent 200. In various embodiments, the ring 210B luminal surface at least partially surrounds the adjacent ring 210A abluminal surface. In various embodiments, the adjacent rings 210A,B are concentric one with another. In other embodiments, the adjacent rings 210A,B are nonconcentric one with another.

In various embodiments, as illustrated in FIG. 2A, the stent 200 is capable of nesting circumferentially. In various embodiments, as illustrated in FIG. 2B, the stent 200 is capable of nesting in a circumferentially non-uniform manner so as to facilitate bending within the vasculature. For example, the stent 200 can nest only along a longitudinal portion thereof that is intended to be oriented on an inner curve within the vasculature. Moreover, the stent 200 can nest differently along its length. For example, it may be desirable for a first portion of the stent 200 to facilitate bending in a first direction, and a second portion of the stent 200 to either facilitate bending in a second direction or remain rigid and not facilitate bending.

Figure 3A:
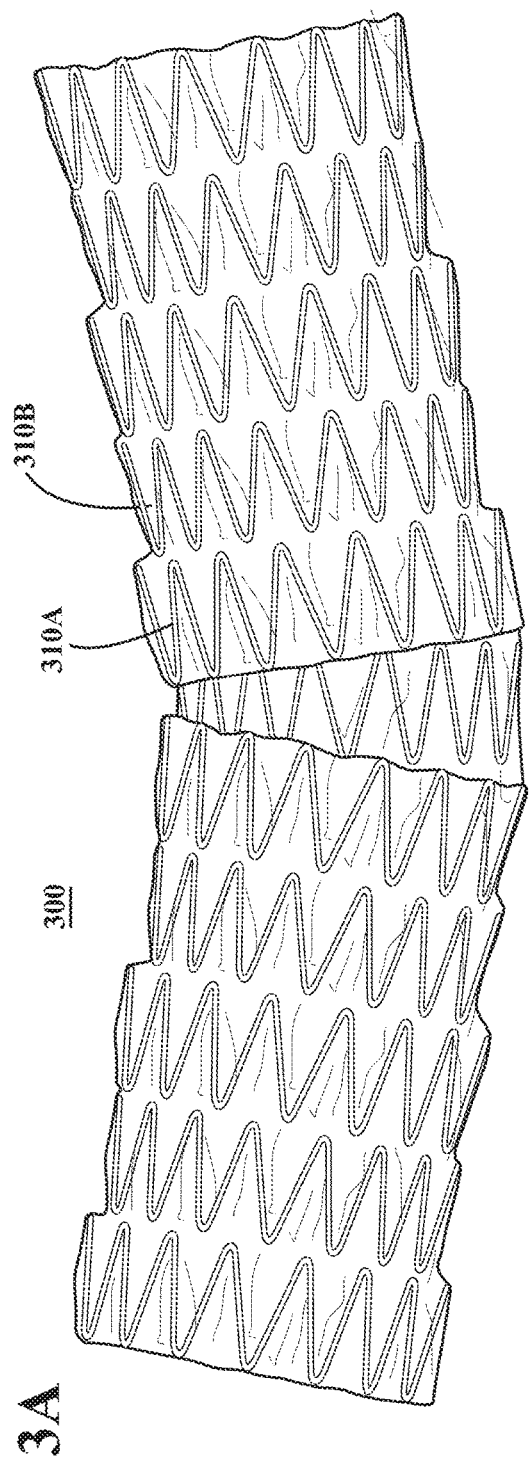
FIG. 3A illustrates a side view of a stent graft comprised of rings having different diameters in accordance with the present disclosure.

Various approaches to nesting are contemplated by the present disclosure, each of which may be used alone or in combination. In various embodiments, adjacent rings 310A,B of a stent 300 can have different diameters, for example, as illustrated in FIG. 3A (refer also to FIG. 1B). More specifically, the ring 310A inner diameter can be greater than the adjacent ring 310B outer diameter. In various embodiments, the ring 310A outer diameter can be less than the adjacent ring 310B inner diameter. The difference between the ring 310A outer diameter and the adjacent ring 310B inner diameter can vary based on stent-graft diameter, wire diameter, graft wall thickness, etc. In embodiments wherein the stent 300 is comprised of a plurality of hoops, one or more adjacent hoops can differ in diameter. In other embodiments wherein the stent 300 has a helical configuration, one or more adjacent helical windings can differ in diameter.

In various embodiments, the ring 310A inner diameter at an edge is greater than the adjacent ring 310B outer diameter at an adjacent edge, while the dimensions of adjacent rings 310A,B of the stent 300 can vary away from their respective edges. For example, and with momentary reference to FIG. 4A, adjacent rings 410A,B,C of a stent 400A can have the same profile and have a larger diameter at one end than another, to thereby facilitate nesting of adjacent rings 410A,B,C. In other embodiments, and with momentary reference now to FIG. 4B, adjacent rings 410D,E,F of a stent 400B can have different profiles and alternate between having a larger diameter at the ends and having a larger in the middle, to thereby facilitate nesting of adjacent rings 410D,E,F. It should be understood that the foregoing are mere examples and should not be construed as limiting the various configurations of adjacent edges having different diameters contemplated by the present disclosure.

Figure 3B:
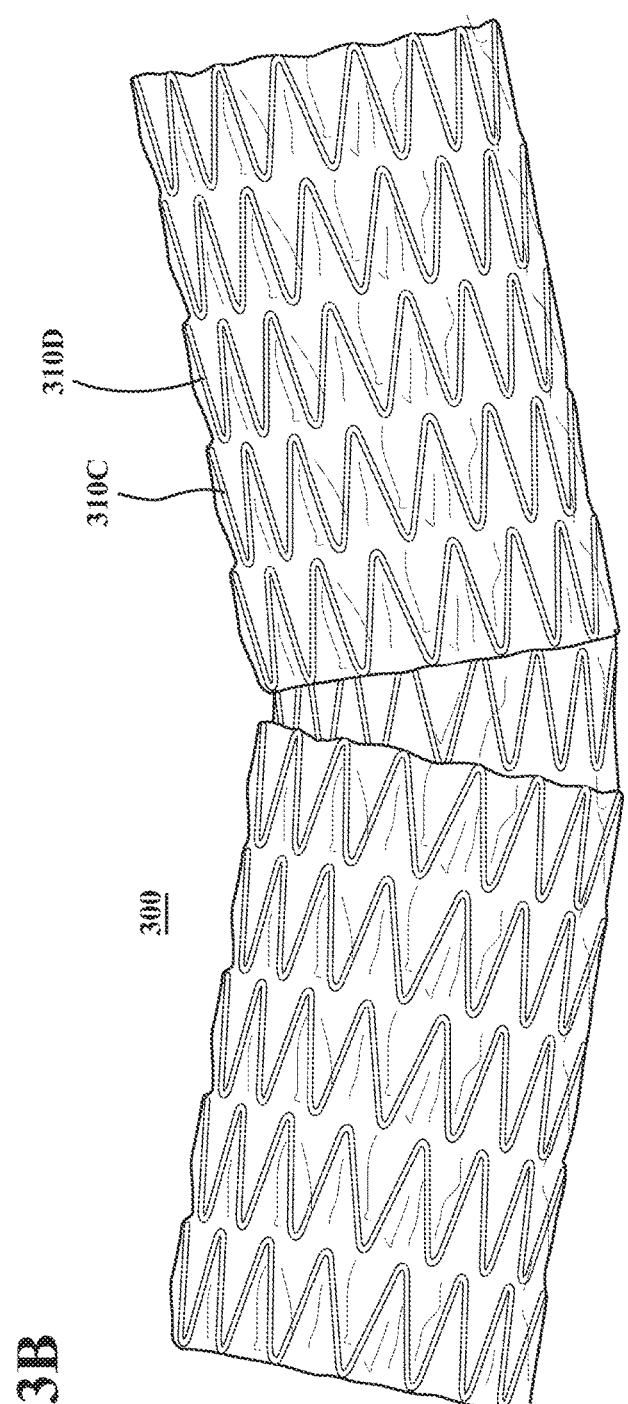
FIG. 3B illustrates a side view of a stent graft comprised of rings having the same diameter in accordance with the present disclosure.

In various embodiments, nesting can be enabled by adjacent rings 310C,D of a stent 300 having the same diameter, for example, as illustrated in FIG. 3B (refer also to FIG. 1A), but different radial strength. Different radial strength can in turn be achieved, inter alia, by the adjacent rings 310C,D having different material properties and/or different non-diameter dimensional characteristics (e.g., different cross-sections), or by manipulating one or more interconnections between the adjacent rings 310C,D. By way of non-limiting example, the adjacent rings 310C,D of the stent 300 may be partially or fully taped by one or more interconnections to thereby couple the adjacent rings 310C,D and/or render them (or one or both of their respective edges) with different radial strength.

In connection with any of the foregoing embodiments, nesting of adjacent rings can be enhanced by incorporating an interconnection in contact with both a ring abluminal surface and an adjacent ring luminal surface, which may assist the ring in "diving" under the adjacent ring to nest therewith. Such an interconnection can be comprised of one or more polymeric materials having resilient properties.

In various embodiments, the materials and components of the stents and interconnections in accordance with the present disclosure can also include one or more bioactive agents. For example, the materials or components can be coated by a therapeutic agent such as, for example, heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, thalidomide, and many others.

Moreover, the materials and components of the stents and interconnections in accordance with the present disclosure can comprise a radio-opaque or echogenic element that enhances imaging or detection during and/or following delivery or deployment. Radio-opaque markers or bands can be comprised of one or more of tungsten, gold, platinum and the like.

The present disclosure also relates to methods of using flexible endoluminal devices capable of bending smoothly. In accordance with various embodiments, an implantable device comprising a stent is restrained or otherwise covered in a radially collapsed delivery configuration by a releasable or removable cover such as a sleeve, sheath, sock or other constraining mechanism. The implantable device is inserted into the vasculature and delivered to a treatment site where it is deployed and assumes a radially expanded configuration. The stent element of the implantable device can be bent smoothly in accordance with the various nesting approaches described supra.

An example of a flexible stent graft was made in the following way: Two sets of NiTi 0.3 mm diameter wire were made by winding 0.3 mm diameter wire in a zig-zag pattern over two stainless steel mandrels 10 mm and 11 mm in diameter respectively. The mandrels with the rings were heated in a convection air oven for 15 minutes at the temperature of 475 degrees Celsius. After the heating, the rings were quenched in a cold water bath to have their shape set at 10 mm and 11 mm inner diameter.

A thin wall ePTFE tube was pulled over an 11 mm diameter stainless steel tubing mandrel. The NiTi rings were placed on top of the ePTFE tubing over the mandrel in an altering fashion—a smaller diameter ring followed by a larger diameter ring in a repetitive way. The 10 mm rings had to be over expended to fit over the mandrel.

The rings were spaced approximately 1 mm apart one from another. Next, the rings were taped with ePTFE film that had FEP on one side. To promote bonding between the rings, the tube and the tape, a compression overwrap was applied.

The assembly was placed in a convection air oven for 30 minutes at the temperature of 320 degrees Celsius. After cooling down the external overwrap was taken off and the device was removed off the mandrel. The smaller 10 mm diameter rings that were overextended while being placed on the 11 mm diameter now returned to their nominal size of 10 mm thus creating alternating smaller and larger segments of the device. The device resulted to be very flexible without tendency to kinking due to nesting of the smaller segments into the larger segments.

It will be apparent to those skilled in the art that various modifications and variations can be made in the present disclosure without departing from the spirit or scope of the disclosure. For example, stents having non-circular cross sections are contemplated by the present disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. An endovascular treatment method, the method comprising:
    delivering an implantable device to a treatment site in a body lumen of a patient, the implantable device including a first ring having a first ring abluminal surface with a first ring outer diameter and a first ring luminal surface with a first ring inner diameter; a second ring adjacent to the first ring and having a second ring abluminal surface with a second ring outer diameter and a second ring luminal surface with a second ring inner diameter, the second ring outer diameter being less than the first ring inner diameter; a third ring adjacent to the second ring, the third ring having a third ring abluminal surface with a third ring outer diameter and a third ring luminal surface with a third ring inner diameter; and an interconnection coupling the first ring and the second ring; and
    bending the implantable device from a non-nested configuration to a nested configuration including the first and second rings nesting with one another.

2. The method of claim 1, wherein in the nested configuration the first ring is nested within the second ring along a longitudinal portion of the first ring that is intended to be oriented on an inner curve of the body lumen.

3. The method of claim 1, including the first ring nesting with in the second ring in a circumferentially non-uniform manner.

4. The method of claim 1, wherein the interconnection is in contact with both the first ring abluminal surface and the second ring luminal surface when the implantable device is in the nested configuration.

5. The method of claim 1, wherein the interconnection is in contact with both the first ring luminal surface and the second ring abluminal surface.

6. The method of claim 1, wherein the interconnection is in contact with both the first ring luminal surface and the second ring luminal surface.

7. The method of claim 1, wherein the interconnection is in contact with both the first ring abluminal surface and the second ring abluminal surface.

8. The method of claim 1, wherein bending the implantable device to the nested configuration includes not producing a kink in the implantable device.

9. The method of claim 1, wherein bending the implantable device from the non-nested configuration to the nested configuration includes bending a first portion of the implantable device in a first direction and bending a second portion of the implantable device in a second direction.

10. The method of claim 1, wherein the interconnection comprises a polymer.

11. The method of claim 1, wherein the first ring luminal surface at least partially surrounds the second ring abluminal surface in the nested configuration.

12. The method of claim 1, wherein the first and second rings are concentric.

13. The method of claim 1, wherein the first and second rings are nonconcentric.

* * * * *